United States Patent [19]

Russ et al.

[11] Patent Number: 5,576,482
[45] Date of Patent: Nov. 19, 1996

[54] PARTICULATE AND FREE WATER CONTAMINATION MEASURING APPARATUS

[75] Inventors: Daniel G. Russ, deceased, late of Fort Wayne, Ind., by Ruth S. Russ, executrix; Karl I. Haddad, Fort Wayne, Ind.

[73] Assignee: Telectro-Mek, Inc., Fort Wayne, Ind.

[21] Appl. No.: 408,340

[22] Filed: Mar. 22, 1995

[51] Int. Cl.$^6$ .................................................. G01N 21/00
[52] U.S. Cl. .................. 73/61.43; 73/64.43; 73/61.59
[58] Field of Search .................... 73/61.59, 64.43, 73/61.43

[56] References Cited

U.S. PATENT DOCUMENTS

| | | |
|---|---|---|
| 617,343 | 1/1899 | Legg . |
| 758,150 | 4/1904 | Schilling . |
| 1,172,728 | 2/1916 | Perkins . |
| 1,834,905 | 12/1931 | Sheldon . |
| 2,144,444 | 1/1939 | Victor . |
| 3,063,289 | 11/1962 | Moul . |
| 3,141,548 | 7/1964 | Newby . |
| 3,500,046 | 3/1970 | Caldwell . |
| 3,510,194 | 5/1970 | Connelly . |
| 3,614,433 | 10/1971 | Caldwell ................ 250/71 G |
| 3,790,279 | 2/1974 | Skala . |
| 3,892,485 | 7/1975 | Merritt et al. . |
| 4,044,604 | 8/1977 | Russ . |
| 4,045,139 | 8/1977 | Russ . |
| 4,090,791 | 5/1978 | Siddigi et al. . |
| 4,193,694 | 3/1980 | Smith . |
| 4,786,473 | 11/1988 | Mukogawa et al. ............ 422/68 |
| 4,944,876 | 7/1990 | Miller . |
| 5,005,430 | 4/1991 | Kibler et al. ............... 43/863.33 |
| 5,190,666 | 3/1993 | Bisconte .................... 210/744 |
| 5,200,064 | 4/1993 | Russ et al. . |
| 5,380,706 | 1/1995 | Himes et al. .............. 507/129 |

OTHER PUBLICATIONS

Millipore Bulletin, Applicatin Guide AG–1, "Analysis and Control of Contamination in Aviation Fuels"; Jan. 22, 1968, Millipore Filter Corporation.

*Primary Examiner*—Hezron E. Williams
*Assistant Examiner*—Jay L. Politzer
*Attorney, Agent, or Firm*—George Pappas

[57] ABSTRACT

A particulate and free water contamination measuring apparatus includes a slide tray adapted for carrying either particulate sample filter elements or free water sample filter elements. The slide tray carrying the filter elements is inserted in a reading chamber whereat, in the particulate mode, the apparatus reads the opacity of two sample filters and, in the free water mode, the apparatus reads fluorescence of the free water filter element. The voltage signals representative of particulates or free water are digitized by an analog to digital converter and read and stored by a digital computer. The digital computer monitors the location of the slide tray within the reading chamber by monitoring location detection switches operable in response to the location of the slide within the reading chamber. The digital computer is programmed to use the digitized voltage signals and compute and provide an output to a liquid crystal display the resulting measured particulates or free water in human readable form, such as a numeric value in milligrams per liter or parts per million.

21 Claims, 6 Drawing Sheets

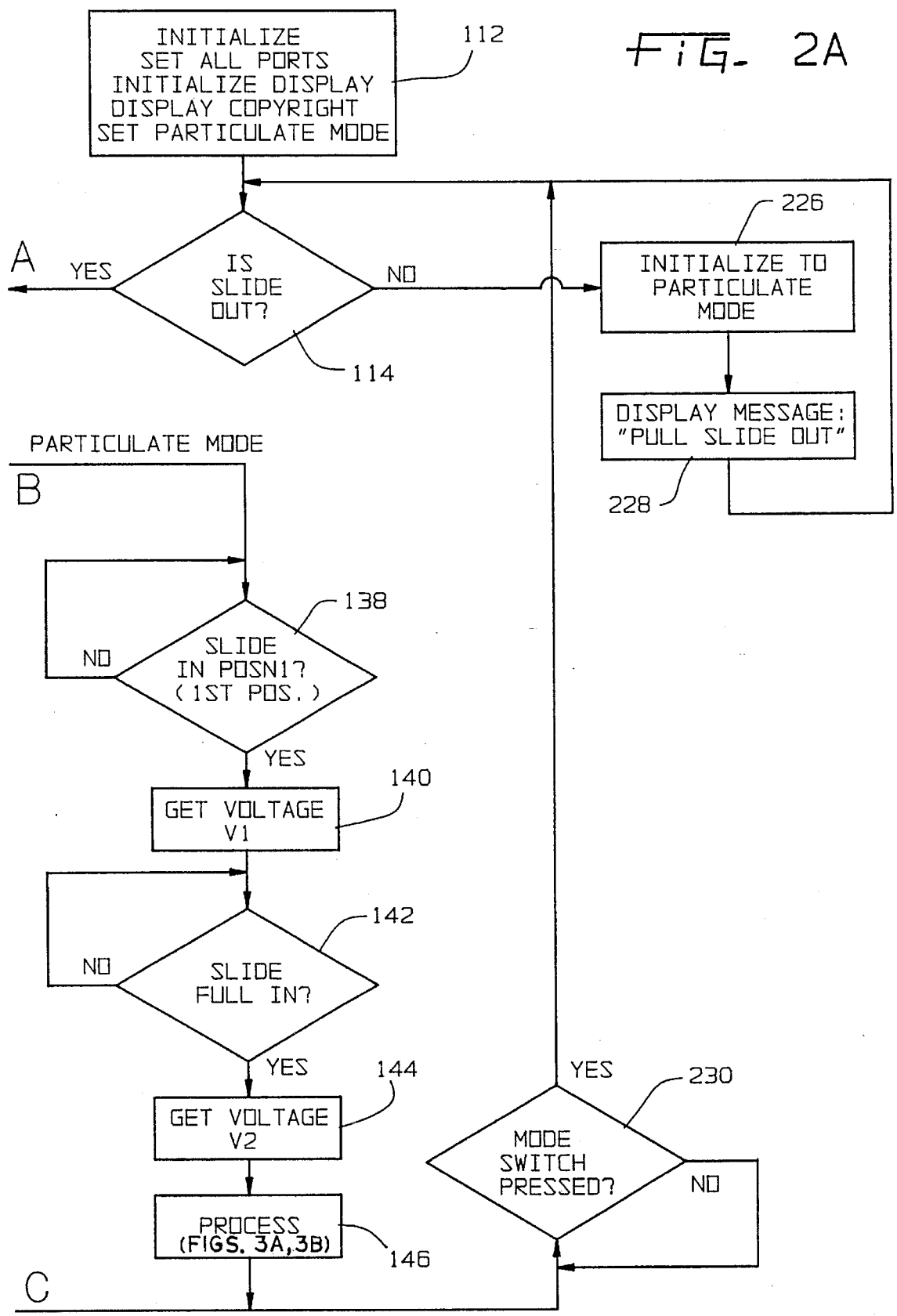

PARTICULATE AND FREE WATER CONTAMINATION MEASURING APPARATUS

TECHNICAL FIELD

The present invention relates to the technical field of fluid contamination detectors for determining acceptable levels of particulate and free water contamination in fluids such as jet fuels. More particularly, the present invention relates to a particulate and free water contamination measuring apparatus through which the operator, after preparation of the sample filter elements or pads, needs only to insert the sample pads into the apparatus and, without any further adjustments, obtains a direct reading on the apparatus display of either the quantity of particulates or volume of free water present in the fuel sample.

BACKGROUND OF THE INVENTION

Numerous different particulate detection and free water detection systems are currently available and are used in laboratories and other locations for determining the contaminate levels in various fluids. One important application is in testing of aircraft and jet fuel for assuring the fuel is within acceptable levels of contaminants. The aircraft or jet fuel must typically be tested for determining whether particulates are below an acceptable value and whether free water in the fuel is below an acceptable value.

Testing of particulate levels has typically been accomplished by obtaining a given volume of the fuel i.e., 700 ml milliliters and forcing the sample fuel through a pair of filter elements of 0.8 micron porosity. The filter elements are placed back to back so that, as the fuel is forced therethrough, the first filter element captures substantially all particulates. However, both of the filter elements are equally exposed to the fuel or other fluid coloration features and, thus, both filter elements obtain the same tint or color dependent on the fuel or fluid coloration. Thereafter, individual opacity readings are taken of the respective filters and the differential between these readings is used as a representative measure of particulate level independent of fuel coloration.

Free water contamination is normally detected by using a single filter element or impregnated with fluorescence which reacts with free water to proportionally fluoresce in the presence of ultraviolet light. Accordingly, the sample fuel i.e., 450 milliliters is passed through the impregnated filter element thereby exposing and allowing any free water to come in contact with the filter element. The filter element is then placed adjacent a ultraviolet light source whereby visible light is emitted and a reading is taken from a photocell such as a photoresistor. The photocell reading is proportionally representative of the free water volume in the fuel convertible to a measure of free water per given fuel volume.

The foregoing method of measuring particulate and free water in fuel and other fluids is known and described in, for example, U.S. Pat. No. 4,044,604 and U.S. Pat. No. 4,200,064 both of which are assigned to the assignee of the present invention. In fact, U.S. Pat. No. 5,200,064 discloses an apparatus through which the readings obtained are readable on a display. Unfortunately, that and prior apparatus require substantial operator intervention, for example, zeroing and calibrating the readings, knowing when to take the readings and converting the various readings to meaningful measurements such as parts per million (PPM) for free water content and milligrams per liter for particulate quantities. Unfortunately, this operator required intervention leaves room for potential error and, thus, inaccurate readings.

Accordingly, a need exists for a particulate and free water contamination measuring apparatus requiring substantially no operator intervention except placement of the free water and particulate test sample filter elements or pads for reading purposes and which therefrom directly displays, in human understandable form, such as for the particulate contamination level in milligrams per liter and the free water contamination in parts per million.

SUMMARY OF THE INVENTION

The present invention overcomes the problems and disadvantages of the above-described prior art fuel contamination detection systems and apparatus by providing an apparatus that requires the operator to only place the particulate test sample filter elements or pads or the free water test sample filter element or pad on a slide tray and insert the same into the reading chamber. From that, the apparatus, without any operator intervention, takes the appropriate readings, converts, stores and manipulates the same as needed and finally displays, in human readable form, a free water or particulate level measurement.

In general, the present invention includes a reading chamber wherein, at a first section, a free water reading is obtained by a photoresistor. An ultraviolet lamp and a calibration pad are placed adjacent the photoresistor whereby a calibration reading can be obtained whenever a free water sample pad is not placed within the first section of the reading chamber. When a free water sample filter pad is placed within the first section of the reading chamber, it blocks the calibration pad from UV light exposure so that the photoresistor is exposed to only the light given off by the free water sample test pad.

The reading chamber further includes a second section for obtaining a particulate reading including an incandescent lamp and phototransistor. The filter elements exposed to the fuel sample are consecutively placed between the incandescent lamp and the phototransistor and the phototransistor outputs which are representative of the opacity of the respective filters are consecutively read for use in calculating the particulate level of contamination. It is noted that, as with other prior art fuel contamination detectors, one of the filter elements includes both the particulates and the coloration of the fuel whereas the other filter element mostly includes the coloration of the fuel. Furthermore, the filter elements for particulate measurements and/or free water measurements are placed on a slide having two apertures and the slide is adapted for insertion within the reading chamber and proper placement of the filter elements within the first and second sections of the reading chamber.

It is noted that when measuring free water, only one of the slide tray apertures are used for placement of the free water filter element and the operator must know which of the two slide apertures the free water filter element must be placed in. In the case of particulate measurement, however, both apertures of the slide are used, one for the filter element which is both colored and contains particulates and the other for the filter element which is only colored.

The present invention further includes location detectors incorporated within the reading chamber and cooperating with the slide tray for providing output indications representative of the slide location within the reading chamber. The preferred location detectors include a plurality of switches preferably in the form of combination of light emitting diodes and photodiodes, each located proximate to the other and adapted for interruption of light to the photodiode by the slide tray. The LED's and photodiodes are located within the reading chamber as needed thereby providing positive outputs representative of the location of the slide tray within the reading chamber.

The present invention further includes a digital computer programmed to operate either in a free water detection mode or a particulate detection mode. The digital computer is programmed to open and close switches for selectively obtaining readings from the output of the phototransistor representative of particulate levels and the output of the photoresistor representative of free water. The analog readings from the phototransistor and photoresistor are converted to digital form via an analog to digital converter and the results thereof are stored by the digital computer. Additionally, the readings from the phototransistor and photoresistor are read by the digital computer depending on the inputs from the location detectors. Thus, the digital computer is programmed to take the proper readings only when the slide tray is in the proper sampling location as determined by the location detectors or switches.

In the case of free water detection, the digital computer is programmed to calculate a quotient equivalent to the voltage output from the photoresistor divided by the slope of a standard Free Water curve, previously calculated from standard readings using the same system and stored in memory. Thereafter, the result is added to a previously stored constant and multiplied with a previously stored free water constant and the result thereof is sent to and displayed on a liquid crystal display in human readable form, namely a numeric value in parts per million.

In the particulate mode, the digital computer is programmed to evaluate the first and second value outputs obtained from the phototransistor and thereafter calculate a quotient Q by dividing the larger of the two values by the smaller. In this fashion, regardless of which of the slide tray apertures the respective particulate sample filter elements are placed, the one with the greatest opacity necessarily being the one representative of only the color and not having particulates thereon (highest opacity) will always be used as the numerator in calculating the quotient Q. Thereafter, the log of Q is calculated and the resultant thereof multiplied with a particulate constant K. The display thereof is then sent to and displayed on the liquid crystal display in human readable form, namely a numeric value in milligrams per liter.

In one form thereof, the present invention is an apparatus for measuring free water contamination of a fluid. The apparatus includes a free water detection means for detecting free water in the fluid and generating an electrical signal proportional to the presence of free water when a filter sample of the fluid is placed proximate thereto. The apparatus also includes a location detection means for generating an electrical signal in response to the filter sample being placed proximate to the free water detecting means. A digital computer is connected to the free water detection means and is also connected to the location detection means. The computer is programmed to read and store a free water value input from the free water detection means in response to a signal from the location detection means. The computer is further programmed to manipulate arithmetically the free water value input with previously stored constants and store the free water resulting value. A display means is provided and is connected to the computer for displaying output from the computer in human understandable form. The computer is programmed to output for display on the display means the free water resulting value.

In one form thereof, the present invention is an apparatus for measuring particulate contamination of a fluid. The apparatus includes a particulate detection means for detecting particulates on a filter element and generating an electrical signal proportional to the presence of particulates when the filter element is placed proximate thereto. A location detection means is also provided for generating a first electrical signal in response to a first filter element placed proximate the detection means and for generating a second electrical signal in response to a second filter element placed proximate to the detection means. A digital computer is provided and is connected to the particulate detection means and to the location detection means. The computer is programmed to read and store a first particulate value input from the particulate detection means in response to the first signal from the location detection means and also for reading and storing a second particulate value input from the particulate detection means in response to the second signal from the location detection means. The computer is also programmed to calculate a quotient by dividing the larger of the first and second particulate value inputs by the smaller of the first and second particulate value inputs and calculating the logarithm of the quotient, multiplying the quotient with a constant and storing the particulate resulting value. A display means is provided and is connected to the computer for displaying output from the computer in human understandable form. The computer is further programmed to output for display on the display means the particulate resulting value.

BRIEF DESCRIPTION OF THE DRAWINGS

The above-mentioned and other features and object of this invention and the manner of obtaining them will become more apparent and the invention itself will be better understood by reference to the following description of embodiments of the invention taken in conjunction with the accompanying drawings wherein:

FIGS. 2a and 2b are a flow chart of the main program of the digital computer;

Corresponding reference characters indicate corresponding parts throughout the several views of the drawings.

The exemplifications set out herein illustrate preferred embodiments of the invention in one form thereof and such exemplifications are not to be construed as limiting the scope of the disclosure or the scope of the invention in any manner.

DETAILED DESCRIPTION OF A SPECIFIC EMBODIMENT

Figure 1:
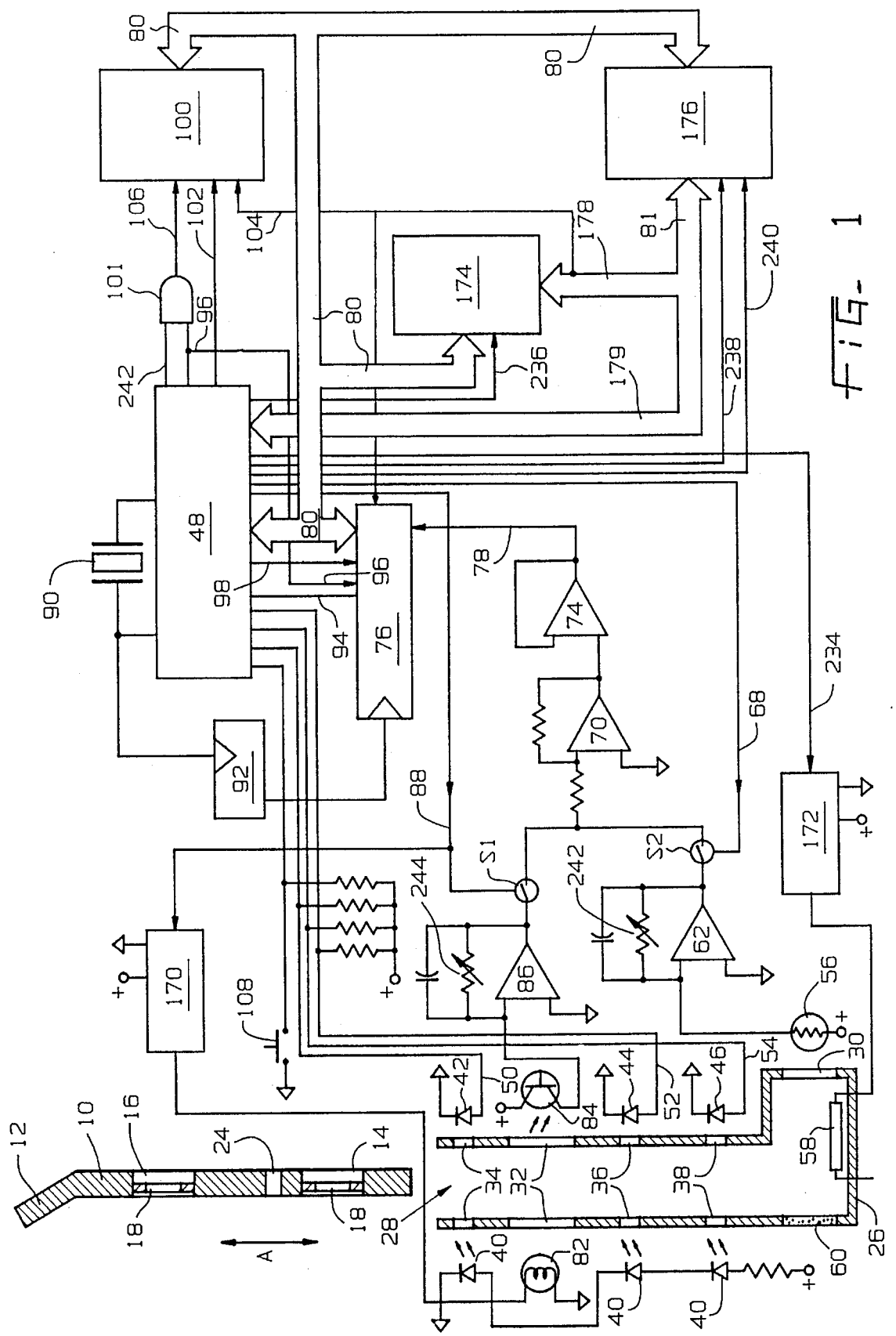
FIG. 1 is an electrical schematic diagram of an apparatus according to the present invention.

Referring initially to FIG. 1, the apparatus includes a slide tray 10 shown in cross section and including a handle portion 12 and first and second filter element apertures 14 and 16. Filter element apertures 14 and 16 are adapted to retain a filter element 18 as shown in a known and customary manner. Slide tray 10 further includes locator aperture 24.

As indicated by arrow A, slide tray 10 is selectively inserted into and withdrawn from reading chamber 26 (shown in cross section) through opening 28. Reading chamber 26 includes a free water reading aperture 30 and aligned particulate reading apertures 32. When slide tray 10 is inserted within reading chamber 26, first filter element aperture 14, first becomes aligned with apertures 32 and, thereafter, as slide tray 10 continues to be inserted further into reading chamber 26, first filter element aperture 14 becomes aligned with free water reading aperture 30 whereas the second filter element aperture 16 becomes aligned with the particulate reading apertures 32.

Reading chamber 26 additionally includes aligned location apertures 34, 36 and 38 located in reading chamber 26 with respect to the location of aperture 24 of slide tray 10 in a manner whereby the location of slide tray 10 can be determined. In this regard, light-emitting diodes 40 are provided on one side of reading chamber 26 near and aligned with location apertures 34, 36 and 38 and photosensors in the form of photodiodes 42, 44, and 46 are provided on the other side of reading chamber 26 near and aligned with location apertures 34, 36, and 38 respectively. As slide tray 10 is inserted within reading chamber 26, the light from light-emitting diodes 40 will either be blocked or allowed to travel through locator aperture 24 of slide tray 10 to photodiodes 42, 44, and 46, thereby providing a low or high signal to digital computer 48 through lines 50, 52, and 54. In this regard, digital computer 48 is programmed to monitor lines 50, 52, and 54 and, depending on the status of each, know the location of the slide tray 10 and performing pre-programmed operations. Digital computer 48 monitors lines 50, 52, and 54 for the following status on each for determining the position of slide tray 10 within reading chamber 26:

| | SLIDE POSITION | | | | |
|---|---|---|---|---|---|
| LINE | A | B | C | D | E |
| 50 | 0 | 1 | 0 | 1 | 1 |
| 52 | 0 | 0 | 1 | 1 | 1 |
| 54 | 0 | 0 | 1 | 1 | 0 |

WHERE POSITION:

A=SLIDE TRAY FULLY RETRACTED FROM READING CHAMBER

B=SLIDE TRAY STARTING TO BE INSERTED WITHIN READING CHAMBER THROUGH OPENING 28 BUT APERTURE 14 NOT YET ALIGNED WITH APERTURE 32

C=SLIDE TRAY APERTURE 14 ALIGNED WITH READING CHAMBER APERTURES 32

D=SLIDE APERTURE 14 INSERTED PAST READING CHAMBER APERTURES 32 BUT NOT YET ALIGNED WITH FREE WATER APERTURE 30

E=SLIDE TRAY 10 FULLY INSERTED AND APERTURE 14 ALIGNED WITH FREE WATER READING APERTURE 30 AND APERTURE 16 ALIGNED WITH PARTICULATE READING APERTURES 32

For free water measurements, a photoresistor 56 is provided adjacent free water reading aperture 30. Additionally, an ultraviolet light lamp 58 is provided within or on the side of reading chamber 26 in a manner whereby UV light can travel to filter element 18 within aperture 14 of slide tray 10 and causing the necessary fluorescence and visible light for detection by photoresistor 56. It is noted that when slide tray 10 is not fully inserted within reading chamber 26 a filter element 60 of known fluorescence is provided for calibration purposes. When slide tray 10 is fully inserted, however, the filter element within aperture 14 blocks calibration element 60 and, thus, only the fluorescence of the filter element within aperture 14 of slide tray 10 is exposed to UV light and creating the visible light for reading by photoresistor 56. UV lamp 58 is powered by a known and customary constant current power source and is selectively turned on and off by a signal output from computer 48 on line 234 connected to solid state relay 172. In this fashion, UV lamp 58 is turned on only when needed in the free water mode and according to the program commands being executed by computer 48.

The voltage signal from photoresistor 56 is applied to the non-inverting input of operational amplifier 62 that amplifies the signal for input into switch S2. The closing and opening of switch S2 is controlled via line 68 by computer 48. The output of switch S2 is buffered through operational amplifier 70 which has an output to inverting operational amplifier 74 and the output thereof is delivered to analog to digital converter 76 via line 78. The output of analog to digital converter 76 is read by the digital computer 48 via databus line 80.

For reading particulate levels on filter elements 18 an incandescent lamp 82 is provided adjacent one of aligned particulate reading apertures 32 and a phototransistor 84 is provided adjacent the other of the two aligned particulate reading apertures 32 of reading chamber 26. Thus, when either of slide tray apertures 14 or 16 are aligned with reading apertures 32, the opacity of the filter elements 18 therein can be translated to a voltage signal output from phototransistor 84. The voltage signal of phototransistor 84 is applied to the non-inverting input of operational amplifier 86 which amplifies the signal. The amplified signal is delivered to switch S1 which is selectively opened and closed by a signal from digital computer 48 through line 88. The output of switch S1 is connected to the output of switch S2 and is buffered by operational amplifier 70. The output of operational amplifiers 70 is inverted by operational amplifier 74 and converted to a digital signal with the analog to digital converter 76 for reading by digital computer 48 via bus line 80. It is noted that line 88 is also connected to and controls the operation of solid state relay 170 which is, in turn, connected to and selectively provides power to lamp 82. Accordingly, lamp 82 is powered only when computer 48 is in the particulate mode and switch S1 is closed.

As mentioned hereinabove, digital computer 48 controls the opening and closing of switches S1 and S2 via respective lines 88 and 68. Additionally, digital computer 48 is provided with a 12 MHz clock 90 for proper timing of operations. A divider network 92 between clock 90 and analog to digital converter 76 provides a clock signal of less than 4 MHz to analog to digital converter 76. Additionally, a busy line 94, read line 96 and high bin line 98 are provided between computer 48 and analog to digital converter 76 for properly reading the digital signals from analog to digital converter 76 on databus 80. High bin line 98 is provided because digital computer 48 is an 8-bit processor whereas analog to digital converter 76 provides a 12-bit output and, therefore, digital computer 78 is programmed to read the high 8-bit byte first and the second low 4-bit byte thereafter by use of line 98.

Databus 80 is also connected to liquid crystal display 100. Digital computer 48 is connected to display 100 through chip select line 102, register select line 104 (via bus 178), and enable line 106. Enable line 106 is derived from digital computer 48 lines 242 and 96 and NAND gate 101. It is noted that register select line 104 provides an indication of whether data or commands are being sent to display 100 and

7 enable line 106 provides an indication that computer 48 is reading or writing to the display 100.

For changing the operation of measurement from particulate to free water or vice versa, a momentary on switch 108 is provided for providing a momentary low signal on line 110 connected to digital computer 48. As more fully discussed hereinbelow, depressing momentary switch 108 causes digital computer 48 to change between particulate and free water modes and to reverse the positions of switches S1 and S2.

The program for system operations is stored in E prom chip 176. E prom 176 is a 27C64 chip with 64K bytes of memory. However, other similar and equivalent memory devices could be used in its place. The operations of EPROM 176 are controlled by chip enable line 238 and read line 240 connected between computer 48 and EPROM 176. Databus 80 is also connected to EPROM 176 so that previously stored program commands can be read by computer 48. In this regard, a 16-bit address bus 81 is used for addressing each of the 64K bytes of memory in EPROM 176. In view of the characteristics of computer 48, address bus 81 is split up between and is made up of the lower 8 bits or lower address bus 178 and the higher 8 bits or upper address bus 179. Upper address bus is directly connected to computer 48 and specific address bits are provided thereon directly from computer 48. The lower address bus 178, however, is fed through bi-directional buffer 174, for example, such as a HC373 chip. Bi-directional buffer 174 is connected to the databus 80 and is controlled by computer 48 via control line 236. Accordingly, for addressing data, computer 48 places the lower 8 bits on databus 80 and the upper 8 bits on address bus 179 and by control operations in a known and customary manner via lower 8 bits are provided through bi-directional buffer 174 and lower address bus 178 to create a 16 bit address bus 81 capable of accessing all memory locations of EPROM 176.

In the preferred embodiment, the following components are utilized although various equivalents are readily available and are known to those skilled in the art. Digital computer 48 is an Intel 80C31 BH microprocessor, the divider network 92 is a HC4020; the analog-to-digital converter is a Maxim 172 manufactured by Maxim Electronics; the liquid crystal display is a H2570 provided by Hitachi; switches S1 and S2 are made by Harris, part DG201CJ and the remaining components are made and are available from a variety of sources known to those skilled in the art.

In operation, the operator seeking to measure particulates or free water in a fuel or other fluid needs merely turn on the apparatus and depress the mode switch 108 so as to place the apparatus in either the particulate measuring mode or the free water measuring mode. For measuring free water contamination, the operator obtains 450 milliliters of fuel and forces it through a filter element 18 impregnated with fluorescence and which is available, for example, from United Catalyst Inc. Thereafter, the exposed filter element is placed in slide aperture 14 and is merely inserted into the reading chamber. Without further input from the operator, the apparatus obtains the necessary reading, manipulates the reading as needed, and displays in human understandable or readable form the quantity of free water in parts per million of the tested fuel.

When testing for particulates, after placing the apparatus in the particulate mode by depressing mode switch 108, the operator obtains and forces 700 milligrams of fuel through a pair of filter elements 18 which are placed back to back. Accordingly, one of the filters captures substantially all of the particulates while both obtain the same coloration of the fuel. The particulate laden filter element is placed in either of the slide apertures 14 or 16 and the remaining filter element is placed in the other of the two slide apertures. Slide tray 10 is then merely inserted into the reading chamber 26 and the apparatus automatically obtains the necessary readings, acts on those readings, and displays on display 100, in human understandable or readable form, particulates in the tested fuel in milligrams per liter or other equivalent weight per volume units.

Figure 2B:
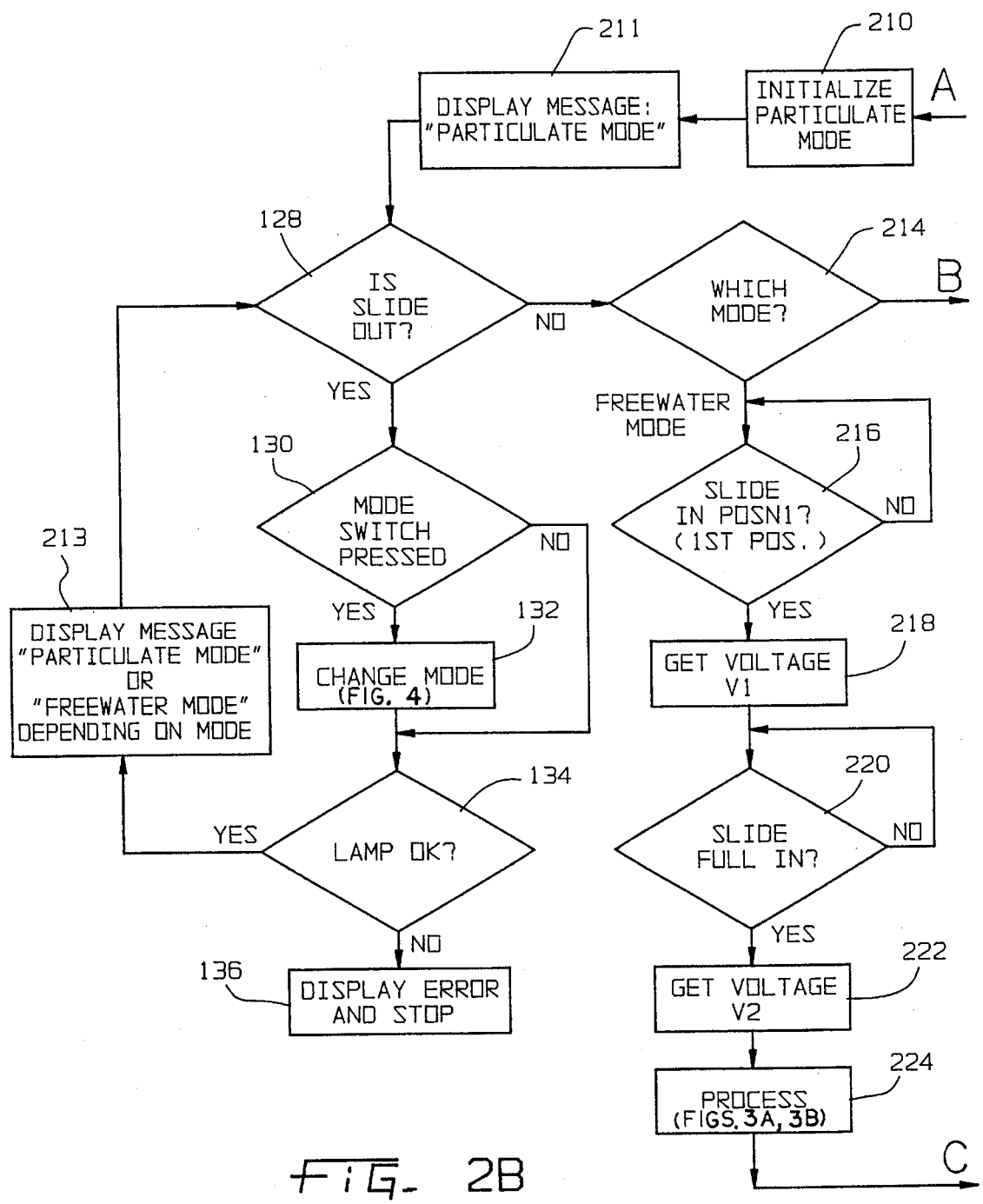

Referring now also to FIGS. 2a, 2b, 3a, 3b and 4, the operation along with the programming flow chart of the apparatus will be described. As shown in FIG. 2a, block 112, upon energizing of the apparatus, initialization takes place during which the ports are all set to zero; the display is initialized by doing a write of spaces; a copyright notice or other pre-programmed message is displayed on the display 100 and; thereafter, the apparatus is set to the particulate mode by closing switch S1 and opening switch S2.

After initialization, as indicated in decision section 114, lines 50, 52 and 54 are monitored for determining the position of the slide tray 10. Anything other than a low signal on all three lines indicating the slide is out indicates that the slide is not out and, therefore, the program moves to the section 226. At 226, computer 48 again sets switches S1 and S2 for particulate mode although this slope is not needed. Thereafter, as shown at block 228, a message "Pull slide out" is displayed and the program returns to decision section 114 whereat lines 50, 52, and 54 are again checked. If all are found to be low, (indicating the slide is out) the program again sets to the particulate mode although this step is also not needed, and as indicated in block 24, displays "Particulate Mode" on the display 100 and moves to decision section 128. Here, lines 50, 52, and 54 are again checked and if the slide continues to be out, moves down to decision section 130 whereat the mode switch flag is checked.

Figure 4:
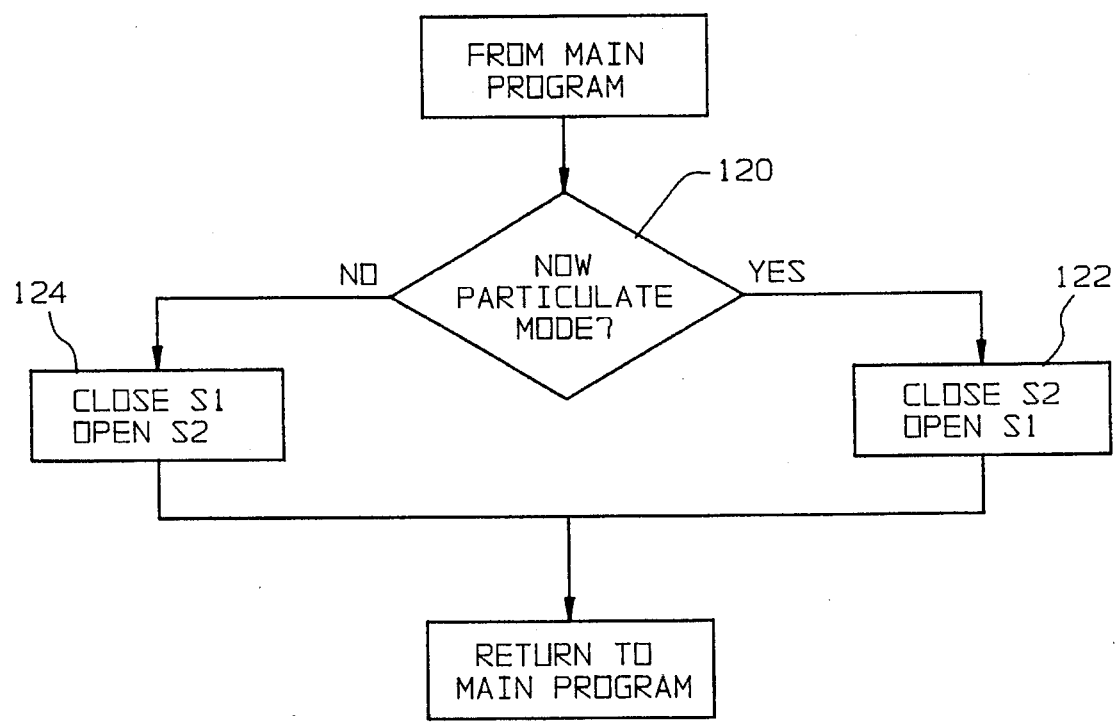

If the mode switch 108 had previously been pressed, the program continues down to the change mode block 132 whereat the change mode routine of FIG. 4 is run. In this regard, as shown in FIG. 4, the change mode routine, in decision section 120, computer 48 checks the prior settings of switches S1 and S2, and thus, whether the current mode is the particulate mode. If currently in the particulate mode, as shown in block 122, switch S2 is closed and switch S1 is opened thereby placing the apparatus in the free water mode. If, however, the unit was not in the particulate mode, as shown in block 124, switch S1 is closed and switch S2 is opened thereby placing the unit in the particulate mode.

If, however, at decision section 130 the mode switch 108 was found not to have been previously pressed, the program continues to decision section 134 whereat the incandescent lamp 82 or the fluorescent lamp 58 is checked for operation. In this regard, if in the particulate mode, switch S1 would be closed and switch S2 would be open and, using a software pause, after a sufficient amount of time has passed for obtaining a stable reading, the digital signal representative of voltage output on line 78 is read through analog to digital converter 76 and databus 80. The value read is compared to a previously stored value, typically at least half of the maximum potential output for phototransistor 84, and if the value read is not greater than the previously stored value, the program moves to block 136 at which point "ERROR" is displayed on liquid crystal display 100 and operation is terminated. If, however, the value received from phototransistor 84 is greater than the previously stored minimum value indicating that incandescent lamp 82 is operating, the program moves to block 213 whereat "Particulate Mode" is displayed on display 100 and then moves back to decision section 128.

It is noted that while in decision section 134, if in the free water mode, switch S1 is open and switch S2 is closed and therefore the signal read by digital computer 48 is the output of the photoresistor 56 which is responsive to the fluorescence of calibration pad 60 from UV lamp 58. The fluorescence of pad 60 provides sufficient visible light for checking whether or not UV lamp 58 is operating and also for providing a voltage signal V1 as discussed hereinbelow. As with the checking of incandescent lamp 82, after pausing and software filtering a sufficient amount of time, a stable signal is provided to line 78 and a digitized signal is read by computer 48. This signal is compared with a previously stored value and if the read value is less than the stored value the program continues to block 136 and "ERROR" is displayed on the display 100 and operations are terminated. Following that check of error, the software filter is more precise to give the free water mode message only when the voltage is at which ppm readings are repeatable. The program then moves to block 213 whereat "Free water Mode" is displayed on display 100 and then continues back to decision section 128.

At decision section 128, unless all of lines 50, 52 and 54 are all low, slide tray 10 is presumed to be at least in part within the reading chamber 26 (position B) and, therefore, the program moves to decision section 214 where it determines whether it is in particulate mode or in free water mode and then moves to section 138 or section 216. In sections 138 and 216, digital computer 48 monitors lines 50, 52, and 54 and waits until slide tray 10 is in the first read position, namely, slide position C described hereinabove wherein tray aperture 14 is aligned with reading apertures 32. It is also noted that, in the interim, computer 48 monitors lines 50, 52 and 54 for a reading of the intermediate position B (not shown in FIGS. 2–4) and if this position is not first read by computer 48 it indicates that the tray is out and stays in decision section 128.

After decision blocks 138, 216, and determining the slide is in the first read position C, the program moves to either blocks 140 or 218 whereat voltage V1 is obtained. Here, depending on whether in the particulate or free water mode, voltage signal V1 is obtained by the output of either phototransistor 84 or photoresistor 56. In the particulate mode, the output of phototransistor 84 and, thus, voltage V1, is representative of the opacity of the filter element placed by the operator in aperture 14 of slide 10. In the free water mode, however, voltage V1 is representative of the fluorescence of calibration pad 60 since slide tray 10 has not yet been fully inserted and pad 60 is still emitting visible light to photoresistor 56. As discussed hereinabove, voltage V1 is obtained through either operational amplifier 62 or 86 and, as described hereinabove, by control of switches S1, S2, etc., which had been set depending on the mode of operation.

After obtaining voltage VI, as indicated in decision section 142 (particulate mode) or 220 (free water mode), lines 50, 52, and 54 are again monitored. Here, lines 50, 52 and 54 are monitored for determining whether the slide tray 10 has been fully inserted to the second position or position E as described hereinabove. The intermediate position D is also monitored for confirming slide location and, unless the intermediate position D and the second read position E are read by computer 48, an error condition will occur and "ERROR" will be displayed on display 100 (not shown in FIGS. 2a and 2b).

When slide tray 10 has been fully inserted and is in the second position E whereat tray aperture 14 is aligned with free water reading aperture 30 and slide tray aperture 16 is aligned with particulate apertures 32, voltage V2 is obtained as indicated by blocks 144 or 222. Voltage V2, again, depending on whether in the particulate or free water mode, is obtained by the voltage output of either phototransistor 84 or photoresistor 56. In the particulate mode, switch S1 would be closed and switch S2 would be open and, thus, the output voltage of phototransistor 84 representative of the opaqueness of filter element 18 in aperture 16 is read and stored by computer 48. It is noted that the filter element 18 in aperture 16 is the second of the two filter elements and may or may not be the filter element laden with particulates. Thus, in the particulate mode, the value of voltage V1 stored by computer 48 may or may not be greater than the value of the stored value for the voltage V2.

In the free water mode, voltage V2 is obtained from photoresistor 56. Because the sample filter element 18 in this case is in aperture 14 of tray 10, it blocks calibration pad 60 and the fluorescence of that sample filter element 18 creating visible light produces the voltage output at photoresistor 56 representative of the sample filter pad 18. Thus, in the free water mode, since switch S2 is closed and switch S1 is open, the value for voltage V2 representative of the sample filter element 18 is stored by computer 48.

Figure 3A:
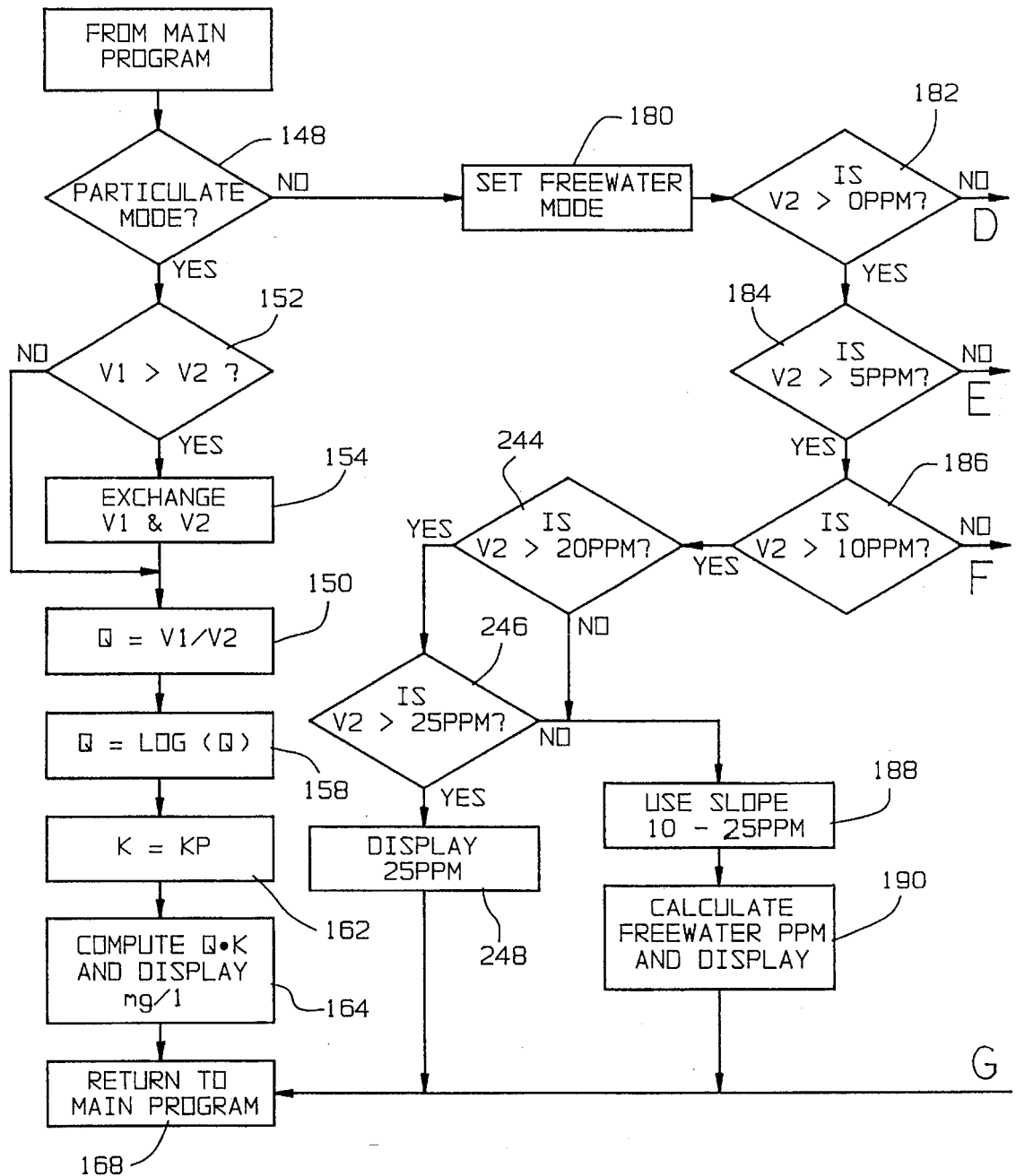
FIGS. 3a and 3b are a flow chart of the process routine called on by the main program of FIGS. 2a and 2b; and, FIG. 4 is a flow chart of a change mode routine called on by the main program of FIGS. 2a and 2b.
Figure 3B:
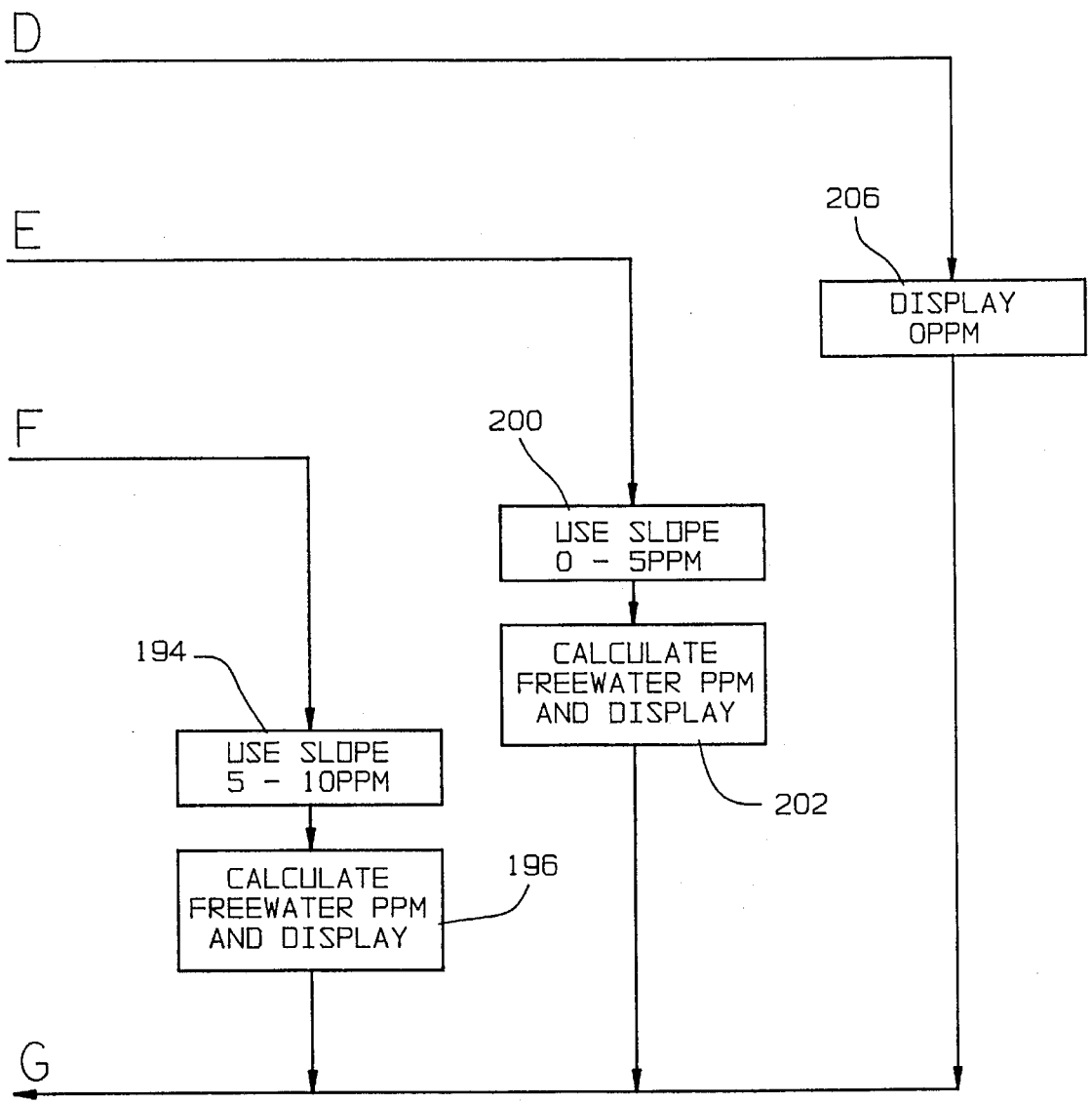

Having obtained and stored values for the voltages V1 and V2, the program moves to the process block or routine 146, 224 as more fully described and shown in FIGS. 3a and 3b. In the process routine, in decision section 148, computer 48 determines if it is in the particulate mode and, if not, immediately travels to block 180 whereat it set to the free water mode, although this is not needed and then goes to section 182.

If at decision section 148 it is determined that the apparatus is in the particulate mode, the program moves to decision section 152 whereat the values of V1 and V2 are compared and if the value of V1 is not greater than V2, the program moves directly to block 150 for calculating the quotient Q. If on the other hand the value of V1 is greater than the value of V2, the program moves to block 154 whereat the values of V1 and V2 are exchanged and, thereafter, continues downward to block 150 for calculating the quotient Q. It is noted that the values of V1 and V2 are compared in decision section 152 because the operator may have placed the particulate laden filter element in either of the slide tray apertures 14 or 16 and, thus, either V1 or V2 could be greater than the other and, further because it is desired that the quotient Q always be greater than 1 for calculating the log of Q as described hereinbelow.

After calculating the log of quotient Q in decision section 158 and storing the new quotient Q in its place, computer 48 again moves directly down to section 162 whereat a constant KP is recalled from storage and stored in K. The particulate constant KP is representative of a conversion factor to convert the quotient Q (16-bit arithmetic result) to the value displayed by display 100 in mg/l. As indicated, the particulate constant KP is stored in place of the variable constant K and, thereafter, as indicated in block 164 the values of the constant K and quotient Q are multiplied and the result thereof is sent to and displayed on display 100 in human readable form and, more particularly, in numeric form and in milligrams per liter. Finally, as indicated in block 168, the program returns to the main program and resumes operations thereat.

If the mode of operation in decision section 148 is free water however, a different process is followed to calculate and display the amount of free water in the fuel in parts per million (PPM). After block 180, in decision section 182, V2 is compared with the volute value representative of a standard 0 PPM (zero PPM) calibration filter element stored in EPROM 176. If V2 is smaller, section 206 is executed displaying 0 PPM on display 100. If V2 is larger, as shown in section 184, it is compared with a voltage representative of a standard 5 PPM calibration filter element MIL-S-81282B which was also previously stored in EPROM 176. If V2 is smaller, section 200 is executed whereat the exact PPM read from the free water filter 18 is calculated by dividing the different between V2 and the voltage of the standard 5 PPM calibration filter element and dividing the result by the slope of the line between 0 PPM and 5 PPM also previously stored in EPROM 176. As indicated in block 200, the result is then added to a first previously stored constant of that line and then multiplied by a second previously stored constant that allows to display the free water content of filter 18 on display 100. If in section 184 V2 is larger, as shown in section 186, it is then compared to a voltage representative of a standard 10 PPM calibration filter element MIL-S-81282B previously stored in EPROM 176. If V2 is greater than 10 PPM, the same process described above in blocks 200 and 202 is repeated in blocks 194 and 196 adding a constant of that line to the result of the division using the slope of the line between 5 and 10 PPM and multiplying by conversion constants. If in section 186 V2 is larger, section 244 is executed and V2 is compared to voltage representative of a standard 20 PPM calibration filter element MIL-S-81282B. If V2 is larger than 20 PPM, process steps 200 and 202 are repeated in 188 and 190 adding the constants of that line to the result of the division using the slope of line between 10 and 20 PPM. If in section 244 V2 is larger, decision section 246 is executed. Here, if V2 is less than 25 PPM the step of blocks 188 and 190 are again performed. If, however, V2 is calculated to be greater than 25 PPM in section 246, block 248 is performed whereby 25 PPM is displayed on display 100.

It is noted that in the free water mode, the value of V2 is not linearly related to the actual volume of free water in the fluid and that, for that reason, different slopes are calculated, stored and used thereby better approximating the actual free water in the fluid in parts per million. Although only three different slopes are stored and used herein, namely, 0–5 PPM, 5–10 PPM, and, 10–25 PPM, it is contemplated that if greater accuracies are required, that smaller intervals of slope can be calculated, stored, and used, for example, 0–1 PPM, 1–2 PPM, etc. It is further noted that in the free water mode, voltage V1 previously obtained and stored, is not used in calculating the free water content of fuel, but rather is only used for determining the proper operation of UV lamp 58 and photoresistor 56.

At the conclusion of the process routine, whether in particulate mode or free water mode and the display of the resultant particulate or free water content, as indicated in block 168, the program returns to the main program whereat as indicated in section 230, computer 48 continues to display the result of the last process routine while monitoring whether or not mode switch 108 has been pressed. Here, the result of the last process routine will continue to be displayed on display 100 until the mode switch 108 is pressed. After mode switch 108 is pressed, the program moves to section 114 whereat the entire program can be repeated for testing for free water or particulate in other fuel or fluid samples. When the result is displayed in both free water mode or particulate mode, pressing switch 108 returns the display and the computer 48 to the pull slide out message and decision section 114.

While the invention has been described as having specific embodiments, it will be understood that it is capable of further modifications. This application is, therefore, intended to cover any variations, uses, or adaptations of the invention following the general principles thereof and including such departures from the present disclosure as come within known or customary practice in the art to which this invention pertains and fall within the limits of the appended claims.

What is claimed is:

1. An apparatus for measuring free water contamination of a fluid, said apparatus comprising:

free water detection means for detecting free water in a sample of the fluid and generating an electrical signal proportional to the presence of free water when the filter sample of said fluid is placed proximate thereto;

location detection means for generating an electrical signal in response to the filter sample being located proximate to said free water detecting means;

digital computer means connected to said free water detection means and to said location detection means, said computer means programmed for reading and storing a free water value input from said free water detection means in response to a signal from said location detection means;

said computer means further programmed to calculate and store a free water resulting value using a stored constant with no operator or calibration intervention; and, said computer means further programmed to calculate a quotient by dividing the larger of said first and second particulate value inputs by the smaller of said first and second particulate value inputs, calculating the logarithm of said display means connected to said computer for displaying output from said computer means in human understandable form, said computer means being programmed to output for display on said display means said free water resulting value.

2. The apparatus of claim 1 wherein said free water detection means includes an ultraviolet light source and a photoresistor adjacent said ultraviolet light source, said free water sample including a chemically treated pad adapted to proportionally fluoresce in the presence of ultraviolet light depending on the exposure to free water, said chemically treated pad placed proximate said photoresistor, and wherein said photoresistor generates said proportional electrical signal.

3. The apparatus of claim 2 further comprising an analog to digital converter between said photoresistor and said computer means whereby said proportional electrical signal is converted from analog to digital form.

4. The apparatus of claim 3 further comprising switch means between said photoresistor and said analog to digital converter for providing selective reading by said computer means of said proportional electrical signal from said analog to digital converter, said switch means connected to and selectively controlled by said computer means.

5. The apparatus of claim 2 wherein said location detection means includes a light source and a location detection photosensor and further comprising a slide element having an aperture whereat said chemically treated pad is carried, said aperture adapted for alignment between said light source and said location detection photosensor when said chemically treated pad is located proximate said ultraviolet light source and said free water detection means photosensor.

6. The apparatus of claim 1 further comprising an analog to digital converter between said free water detection means and said computer means whereby said proportional electrical signal is converted from analog to digital form.

7. The apparatus of claim 1 further comprising switch means between said free water detection means and said computer means for providing selective reading of said proportional electrical signal by said computer means, said switch means connected to and controlled by said computer means.

8. The apparatus of claim 1 wherein said location detection means includes a light source and a location detection photosensor and further comprising a slide element having an aperture whereat said fluid filter sample is carried, said aperture adapted for alignment between said light source and said location detection photosensor when said fluid sample is located proximate said free water detection means.

9. The apparatus of claim 8 wherein said location detection photosensor is a phototransistor.

10. An apparatus for measuring particulate contamination of a fluid, said apparatus comprising:

particulate detection means for detecting particulates on a filter element and generating an electrical signal proportional to the presence of particulates when said filter element is placed proximate thereto;

location detection means for generating a first electrical signal in response to a first filter element being placed proximate said detection means and for generating a second electrical signal in response to a second filter element being placed proximate said detection means;

digital computer means connected to said particulate detection means and to said location detection means, said computer means programmed for reading and storing a first particulate value input from said particulate detection means in response to said first signal from said location detection means and, further, for reading and storing a second particulate value input from said particulate detection means in response to said second signal from said location detection means;

said computer means further programmed to calculate a quotient by dividing the larger of said first and second particulate value inputs by the smaller of said first and second particulate value inputs, calculating the logarithm of said quotient, multiplying said quotient with a constant, and storing the particulate resulting value with no operator or calibration intervention; and, a display means connected to said computer means for displaying output from said computer means in human understandable from, said computer means being programmed to output for display on said display means said particulate resulting value.

11. The apparatus of claim 10 wherein said particulate detection means includes a light source and a phototransistor adjacent said light source, said filter elements adapted for being placed between said light source and said phototransistor, whereby said phototransistor generates said first and second electrical signals proportional to the presence of particulates.

12. The apparatus of claim 11 further comprising an analog to digital converter between said phototransistor and said computer means whereby said proportional electrical signals are converted from analog to digital form.

13. The apparatus of claim 12 further comprising switch means between said phototransistor and said analog to digital converter for providing selective reading of said proportional electrical signals by said analog to digital converter, said switch means connected to and controlled by said computer means.

14. The apparatus of claim 13 wherein said location detection means includes first and second light sources and first and second location detection photosensors and, further, comprising a slide element having two apertures and adapted for supporting a first and a second filter element, said first slide aperture adapted for alignment between said first light source and said first location detection photosensor when said first filter element is located between said detection means light source and photosensor and wherein said second aperture is adapted for alignment between said second light source and said second location detection photosensor when said second filter element is located between said detection means light source and photosensor, whereby said first electrical signal is generated by said detection means photosensor in response to said first filter element and said second electrical signal is generated by said detection means photosensor in response to said second filter element.

15. The apparatus of claim 14 wherein said first and second location detection means photosensors are phototransistors.

16. The apparatus of claim 10 further comprising an analog to digital converter between said particulate detection means and said computer means whereby said proportional electrical signals from said particulate detection means are converted from analog to digital form.

17. The apparatus of claim 10 further comprising switch means between said particulate detection means and said computer means for providing selective reading of said proportional electric signals by said computer means, said switch means connected to and controlled by said computer means.

18. The apparatus of claim 10 further comprising:

free water detection means connected to said computer means for detecting free water in the fluid and generating an electrical signal proportional to the presence of free water when a sample of said fluid is placed proximate thereto;

wherein said location detection means generates an electrical signal in response to a fluid sample being placed proximate to said free water detection means;

said computer means being further programmed for selectively operating in a free water mode wherein said computer means reads and stores a free water value input from said free water detection means in response to a signal from said location detection means;

said computer means further programmed to calculate and store a free water resulting value using a stored constant; and, said computer means further programmed to output for display on said display means said free water resulting value.

19. The apparatus of claim 18 wherein said free water detection means includes an ultraviolet light source and a photoresistor adjacent said ultraviolet light source, said free water sample including a chemically treated pad adapted for proportional fluorescence in the presence of ultraviolet light depending on the exposure to free water, said chemically treated pad placed proximate said photoresistor and wherein said free water detection means photoresistor generates said free water proportional electrical signal; and, wherein said particulate detection means includes a light source and a phototransistor adjacent said light source, said filter elements adapted for being placed between said light source and said phototransistor, whereby said particulate phototransistor generates said first and second electrical signals proportional to the presence of particulates.

20. The apparatus of claim 19 further comprising switch means between said free water detection means and said particulate detection means for providing selective reading of said proportional electrical signals generated by said free water detection means and said particulate detection means, said switch means connected to and controlled by said computer means whereby a free water electrical proportional signal or a particulate proportional electrical signal are selectively read and stored by said computer means depending on said computer mode of operation.

21. The apparatus of claim 20 further comprising an analog to digital converter between said computer means and said free water detection means and said particulate detection means whereby said proportional free water and particulate electrical signals are converted from analog to digital form.

* * * * *

UNITED STATES PATENT AND TRADEMARK OFFICE
CERTIFICATE OF CORRECTION

PATENT NO. : 5,576,482
DATED : November 19, 1996
INVENTOR(S) : Daniel G. Russ et al.

It is certified that error appears in the above-identified patent and that said Letters Patent is hereby corrected as shown below:

Col. 7, line 11, change "E prom" to --EPROM--
Col. 7, line 12, change "E prom" to --EPROM--

Signed and Sealed this

Eighteenth Day of February, 1997

Attest:

Attesting Officer

BRUCE LEHMAN

Commissioner of Patents and Trademarks